United States Patent [19]

Estreicher et al.

[11] Patent Number: 4,504,304
[45] Date of Patent: Mar. 12, 1985

[54] 6-OXABICYCLO(3.2.2.)NONAN-4-OL ETHER HERBICIDES

[75] Inventors: Herbert Estreicher; George B. Payne, both of Modesto, Calif.

[73] Assignee: Shell Oil Company, Houston, Tex.

[21] Appl. No.: 527,045

[22] Filed: Aug. 29, 1983

[51] Int. Cl.³ ............... A01N 9/00; C07D 313/08
[52] U.S. Cl. ................................. 71/88; 549/60; 549/355; 549/283; 548/127; 548/128; 548/135; 548/136; 548/203; 548/206; 548/235; 548/247; 548/256; 548/262; 548/336; 548/374; 548/525; 546/152; 546/139; 546/269; 544/182; 544/215; 544/335; 71/95; 71/94; 71/93; 71/92; 71/90; 71/76
[58] Field of Search ............... 549/355, 60; 546/269, 546/152, 139; 71/88, 76, 90, 92, 93, 94, 95; 544/335, 215, 182; 548/336, 256, 262, 127, 128, 135, 136, 374, 525, 247, 235, 206, 203

[56] References Cited

U.S. PATENT DOCUMENTS 2,511,891  6/1950  Whetstone .................. 549/355
3,506,687  4/1970  Wilson et al. ............... 549/355
3,755,365  8/1973  Fentiman, Jr. et al. ........ 549/355

Primary Examiner—Nicky Chan

[57] ABSTRACT

Novel compounds of the formula

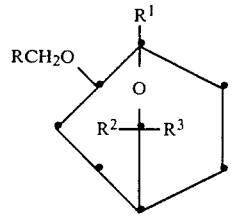

wherein $R^1$, $R^2$ and $R^3$ are H or alkyl and R is an optionally-substituted unsaturated, cycloalkyl, secondary-alkyl, aromatic or heterocyclic group, are useful as plant growth regulators and herbicides. Certain intermediates are also novel.

14 Claims, No Drawings

6-OXABICYCLO(3.2.2.)NONAN-4-OL ETHER HERBICIDES

BACKGROUND OF THE INVENTION

1. Field of the Invention

The present invention relates to novel 6-oxabicyclo[3.2.2]nonan-4-ones, their corresponding alcohols and ethers, to use of the ethers for controlling plant growth and as herbicides and to herbicidal and plant growth regulating compositions containing these novel ethers.

2. Summary of the Invention

The present invention is directed to novel compounds of the formula I

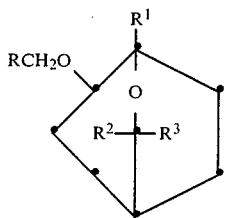

wherein $R^1$, $R^2$ and $R^3$ each independently is a hydrogen atom or an alkyl group containing from 1 to 10 carbon atoms and R is an optionally-substituted unsaturated group containing up to 4 carbon atoms, a cycloalkyl group containing from 3 to 10 carbon atoms, a secondary alkyl group containing from 3 to 10 carbon atoms, or an aromatic or heterocyclic group containing up to 14 carbon atoms. The compounds are useful as herbicides and to control the growth of plants.

Non-limiting examples of species of the compounds of formula I of the invention include:

4-(2-fluorobenzyloxy)-5,7,7-triethyl-6-oxabicyclo[3.2.2]nonane,
4-(2-pyridinylmethoxy)-5,7,7-trimethyl-6-oxabicyclo[3.2.2]nonane,
4-(2-methylbenzyloxy)-7,7-dimethyl-5-ethyl-6-oxabicyclo[3.2.2]nonane,
4-(2-propynyloxy)-5,7,7-trimethyl-6-oxabicyclo[3.2.2]nonane,
4-(2-pyrimidinylmethoxy)-5,7,7-trimethyl-6-oxabicyclo[3.2.2]nonane,
4-(tetrahydro-2-pyranylmethoxy)-5,7,7-trimethyl-6-oxabicyclo[3.2.2]nonane.

In the derivatives of formula I, preferably each $R^1$, $R^2$ and $R^3$ is independently a hydrogen atom, a methyl group or an ethyl group. In one embodiment of the invention, each $R^1$, $R^2$ and $R^3$ is the same and is preferably a methyl group.

In the derivatives of formula I, preferably R is an ethynyl group, a 2-pyridinyl group or a phenyl group optionally substituted by 1 or 2 chlorine or fluorine atoms or methyl groups. In one embodiment of the invention, R is a 2-chlorophenyl, a 2-fluorophenyl, a 2-methylphenyl group or a phenyl group.

Compounds that possess substantially the same plant growth regulator or herbicidal utility as those of formula I described herein and which can be prepared in like manner are equivalents thereof and include compounds wherein, for example, R is an unsaturated, aromatic or heterocyclic moiety, or cyclopropyl or 1-methylcyclopropyl, including but not limited to cyano, naphthyl, imidazolyl, triazolyl, thiadiazolyl, 2-quinolinyl, 1-isoquinolinyl, pyrrolyl, cyclohexenyl, N-methylimidazol-2-yl, N-methylpyrazol-2-yl, isoxazolyl, oxazolyl, isothiazolyl, thiazolyl, thienyl, 5-methyl-2-furanyl, triazinyl, pyrimidinyl, and the like.

The derivatives of formula I of the invention exhibit geometrical and optical isomerism and may be prepared in geometrical and/or optical forms, and as racemates. The various individual optical and geometrical forms and various combinations of the derivatives of the invention usually have some difference in herbicidal or plant growth control properties. The present invention contemplates all these active forms. The derivatives of formula I that have the $RCH_2O$ group syn (with respect to the oxygen bridge) usually have the highest activity. Moreover, the derivatives of the formula I of the inventions also are useful as solvents or dispersing agents, e.g. for paints, pigments, polymers and synthetic fibers, and as plastisizers, e.g. for vinyl resins. These latter uses are irrespective of stereoisomerism.

The derivatives of formula I of the invention are prepared by an etherification reaction which introduces the group $CH_2R$. The etherification is conducted by treating the corresponding 6-oxabicyclo[3.2.2]nonan-4-ol derivative with a compound of the formula $RCH_2X$ in which R is defined as in formula I above and X is a halogen atom, such as bromine, chlorine or iodine, or is a mesyloxy, tosyloxy group or the like, in the presence of a base and, preferably, an inert diluent. The base is suitably an alkali metal hydride, hydroxide or carbonate, including, for example, sodium hydride, sodium hydroxide, potassium carbonate and the like. Inert diluents (solvents) are suitably organic solvents, such as ethers, aromatic hydrocarbons and the like, including, for example, diethyl ether, tetrahydrofuran, dimethyl sulfoxide, toluene, methylene chloride and the like. The reaction is usually carried out under normal pressures and ambient temperatures. Suitable temperatures of the reaction include those from about 0° C. to about 120° C., preferably from about 20° C. to about 100° C. The reaction can be conducted in a two-phase system preferably in the presence of a phase-transfer catalyst. For example, such a system is an aqueous sodium or potassium hydroxide solution with toluene or methylene chloride with a catalyst, such as an ammonium compound, including tetra-n-butylammonium chloride, bromide or hydrogen sulfate, triethylbenzylammonium chloride and the like.

The derivatives of formula I are recovered and isolated by conventional techniques.

The corresponding 6-oxabicyclo[3.2.2]nonan-4-ols and 6-oxabicyclo[3.2.2]nonan-4-ones are also novel derivatives and have the formula II

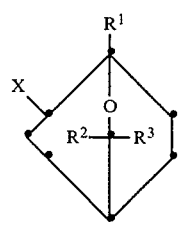

wherein each $R^1$, $R^2$ and $R^3$ is independently a hydrogen atom or an alkyl group containing from 1 to 10 carbon atoms; and X is —OH or =O. In the novel derivatives of formula II, preferably each $R^1$, $R^2$ and $R^3$ is independently a hydrogen atom, a methyl or ethyl group. In one embodiment of the invention, $R^1$, $R^2$ and $R^3$ are the same and preferably each is a methyl group.

The derivatives of formula II are prepared by multi-step conventional procedures known in the art from a 2-oxocyclopentanecarboxylic acid ester. This known ester is subjected to Michael addition in toluene with an alkyl vinyl ketone, e.g., at room temperature in the presence of triethylamine similar to the method of Dauben, W. G., et al, JACS, (1960), 82, page 4245. The resulting addition product is cyclized, e.g., at room temperature with sulfuric acid similar to the method of Evans, et al.. *J. Chem. Soc. Chem. Comm.*, (1982) page 1342, to give the novel lactones of the formula III

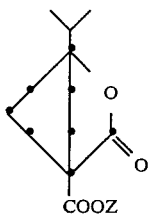

III in which Z is the residue of an esterifying group, and Y is an alkyl group containing from 1 to 4 carbon atoms. Any esterifying group, organic or inorganic, which will not interfere with the reaction can be used for Z. For convenience, Y and Z each independently is an alkyl group containing from 1 to 10 carbon atoms. For example, Y and Z each independently is a methyl or ethyl group. In one embodiment of the invention, Y is a methyl group and Z is an ethyl group.

The lactone of formula III is treated with a strong acid at elevated temperature to give a mixture of unsaturated cycloheptenyl diesters, which are mono-decarboxylated, e.g., by treatment with aqueous sodium chloride and dimethyl sulfoxide at elevated temperatures. The resultant corresponding mixture of unsaturated mono-esters is treated with an appropriate Grignard reagent, e.g., alkylMgBr, in which the alkyl portion corresponds to one of the geminal alkyl substituent desired at the 7 position in formula II to give a mixture containing, e.g., the alpha,alpha,5-trialkyl-5-cyclohep-tene-1-methanol derivative.

This alcohol mixture is epoxidized and cyclized, e.g., by treatment with a peroxy acid followed by an acid, such as p-toluene-sulfonic acid, to give on separation the desired 6-oxabicyclo[3.2.2]nonan-4-one of formula II, which is converted into the corresponding exo-alcohol, a 6-oxabicyclo[3.2.2]nonan-4-ol, e.g., by treatment with a suitable agent, such as L-selectride. This ketone also is converted into predominantly the endo-alcohol by reduction, e.g., with sodium borohydride in ethanol.

One alternative procedure, is to start from cyclopentanone itself. After its Michael addition with an alkyl vinyl ketone as described above, the resulting product is cyclized with sulfuric acid as described above to give a lactone which is heated with acid and ethanol to give the ring-cleaves mixture of desired ethyl 3- (and 4-)cycloheptenecarboxylates for subsequent treatment with Grignard reagent, epoxidation and cyclization as described above to yield the desired alcohol of formula II.

The invention also includes a method of influencing agent growth and combatting unwanted plants which comprises applying to the locus an effective amount of a compound of Formula I. For example, the compounds of formula I can change plant morphology, depress the growth of plants, inhibit germination or totally or selectively kill plants depending on the amounts used. For application, the compound generally is applied most effectively by formulating it with a suitable inert carrier or surface-active agent, or both. The invention, therefore, also includes compositions suitable for influencing plant growth and combatting unwanted plants, such compositions comprising an inert carrier or surface-active agent, or both, and as active ingredient at least one compound of Formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs: magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone, isophorone, and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds, Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Influencing plant growth or protection of a locus or area from undesirable plants is effected by applying a compound of Formula I, ordinarily in a composition of one of the aforementioned types, to soil in which the seeds of the (unwanted) plants are present, or to the foliage of the (unwanted) plants. The active compound, of course, is applied in an amount sufficient to exert the desired action.

The amount of the compound of the invention to be used in influencing plant growth or combating undesired plants will naturally depend on the condition of the plants, the degree of activity desired, the formulation used, the mode of application, the climate, the season of the year, and other variables. Recommendations as to precise amounts are, therefore, not possible. In general, however, application to the locus (to be protected) of from 0.1 to 10.0 kg per hectare of the compound of Formula I will be satisfactory.

ILLUSTRATIVE EMBODIMENTS

The invention is illustrated by the following embodiments which describe the preparation of typical species of the invention. The embodiments are for illustration and should not be regarded as limiting the invention in any way. The identity of the products, including intermediates, was confirmed by elemental, infrared nuclear magnetic resonance spectral (NMR) or mass spectral analyses as necessary.

EMBODIMENT 1

Ethyl 2-oxo-1-(3-oxobutyl)cyclopentancarboxylate (A.) A literature procedure of Dauben et al, *J.A.C.S.*, 82, page 4245 (1960) was modified as follows. A solution of 75.8 g of ethyl 2-oxocyclopentanecarboxylate, 50 ml of methyl vinyl ketone, 250 ml of toluene and 18 ml of triethylamine was allowed to stand for 4 days at 25° C. Concentration, followed by Claisen distillation gave 100.1 g of product (98% purity), b.p. 100°–105° C. (0.2 mm).

(B.) A mixture of 102.0 g of ethyl 2-oxocyclopentanecarboxylate, 300 ml of benzene, 67 ml of methyl vinyl ketone and 20 ml of triethylamine was allowed to stir magnetically at reflux for 2.5 hours. Concentration followed by Claisen distillation gave 128 g of product.

EMBODIMENT 2

1-(Ethoxycarbonyl)-4-hydroxy-4-methylcycloheptanecarboxylic Acid Lactone

To a stirred solution of 41.0 g of ethyl 2-oxo-1-(3-oxobutyl)-cyclopentanecarboxylate in 20 ml of diethyl ether was added dropwise at 10°–20° C. a 60 ml portion of 95% sulfuric acid. After 18 hours, the mixture was poured onto ice, stirred, and then extracted twice with diethyl ether. The combined ether extracts was washed with saturated bicarbonate solution, then with water, and dried. Vacuum-concentration gave 31.6 g of product, m.p. 48°–53° C.

EMBODIMENT 3

Following procedures similar to those described in Embodiment 1 and 2 above, 1-(ethoxycarbonyl)-4-hydroxy-4-ethylcycloheptanecarboxylic acid lactone is prepared from ethyl vinyl ketone.

EMBODIMENT 4

Diethyl 4-Methyl-3-Cycloheptene-1,1-dicarboxylate and Diethyl 4-Methyl-4-Cycloheptene-1,1-dicarboxylate To a solution of 32.2 g of 1-(ethoxycarbonyl)-4-hydroxy-4-methylcycloheptanecarboxylic acid lactone of Embodiment 2 above in 300 ml of ethanol was added 12 g of p-toluenesulfonic acid monohydrate and the mixture was stirred at reflux for 64 hours. The cooled mixture was treated with 6.0 g of anhydrous sodium acetate, stirred for 15 minutes, and vacuum-concentrated at 60° C. The residue was shaken with methylene chloride and water, and the methylene chloride extract was washed with saturated sodium bicarbonate solution and dried. Claisen distillation gave 26.1 g of product, b.p. 87°–98° C. (0.2 mm).

EMBODIMENT 5

Ethyl 4-Methyl-3-cycloheptenecarboxylate and Ethyl 4-Methyl-4-cycloheptenecarboxylate To a 2 liter, 3-neck, roundbottom flask equipped with a stirrer, thermometer and 1 ft Snyder column with Claisen head at the top were charged 144 g of a mixture of the dicarboxylates of Embodiment 4 above, 700 ml of dimethyl sulfoxide, 67 g of sodium chloride and 32 ml of water. The reaction mixture was stirred at reflux with 14 ml of distillate being removed over a five hour period as the flask temperature increased from 159° C. to 165° C. The Snyder column was replaced with a condenser and reflux was continued overnight. After 16 hours, the kettle temperature was 162° C. The Snyder column was again attached and an additional 27 ml of distillate was removed over a 7 hour period. The kettle temperature rose slowly to 178° C. during this time. The cooled mixture was poured into water, and extracted twice with hexane, and the combined hexane extracts was washed, dried, concentrated and Claisen-distilled to give 67.6 g of product, b.p. 68°-80° C. (1.0 mm). The isomer ratio was approximately 1:1.

EMBODIMENT 6

α,α-4-Trimethyl-3(and 4)-cycloheptenemethanol

To a stirred mixture of 160 ml of 2.9M methyl magnesium chloride (in tetrahydrofuran) and 350 ml of dry tetrahydrofuran was added dropwise over 30 minutes at 25°-40° C. a solution of 34.0 g of the mixture of monocarboxylates of Embodiment 5 above in 100 ml of tetrahydrofuran. After an additional hour at reflux, the mixture was cooled and treated with 500 ml of water. This mixture was extracted three times with diethyl ether, and the combined extracts was dried, filtered, concentrated and distilled through a micro Vigreaux column to give 27.9 g of product, b.p. 70°-72° C. (0.2 mm), as an about 1:1 mixture of isomers.

EMBODIMENT 7

3,4-Epoxy-α,α,4-trimethylcycloheptanemethanol and 4,5-Epoxy-α,α,4-trimethylcycloheptanemethanol To a stirred ice cold mixture of 67.2 g of the mixture of alcohols of Embodiment 6 above, 1000 ml of methylene chloride and 600 ml of 1M sodium bicarbonate was added portionwise over 40 minutes 92 g of m-chloroperbenzoic acid. The temperature was held below 7° C. After an additional 2.5 hours in the cold, the layers were separated and the aqueous layer was extracted with 200 ml of methylene chloride. The combined methylene chloride extracts was washed twice with 250 ml portions of dilute potassium carbonate and then with 250 ml of 5% sodium hydroxide. Drying and concentration followed by Claisen-distillation gave 66.4 g of product, b.p. 80°-84° C. (<0.1 mm).

EMBODIMENT 8

5,7,7-Trimethyl-6-oxabicyclo[3.2.2]nonan-4-one

To a stirred solution of 66.4 g of the mixture of epoxy alcohols of Embodiment 7 above in 700 ml of methylene chloride was added dropwise over 20 minutes at ambient temperature a solution of 2.0 g of p-toluenesulfonic acid in 25 ml of glyme. The temperature went from 18° C. to 24° C. during the addition. After four hours longer, the solution was washed twice with dilute carbonate and dried. Concentration gave 67.9 g of a pale yellow oil (A). This crude oil product was oxidized as follows:

To a stirred solution of 56.0 g of oxalyl chloride in 800 ml of methylene chloride was added dropwise at −60° C. a solution of 78.0 g of dimethyl sulfoxide in 100 ml of methylene chloride. After an additional 10 minutes, a solution of the above pale yellow oil (A) in 200 ml of methylene chloride was added at −60° C. After 15 minutes longer, 180 g of triethylamine was added dropwise at −60° C. The cooling bath was removed and the mixture was allowed to warm to 0° C. over 45 minutes. A 1 liter portion of water was added and stirring was continued at 25° C. for 15 minutes. The methylene chloride layer was separated, the aqueous layer was extracted twice with methylene chloride, and the combined methylene chloride extracts was washed, dried and concentrated to a residue of 82 g. This was distilled through a spinning band column to give the following:

| Cut | B.p. °C. | (mm) | Weight, grams |
| --- | --- | --- | --- |
| 1 | 40–56 | (1.5) | 3.4 |
| 2 | 56–71 | (1.5) | 10.2 |
| 3 | 71–76 | (1.5) | 6.2 |
| 4 | 76–82 | (1.5) | 11.6 |
| 5 | 82–80 | (1.5–0.1) | 7.8 |

Cuts 2 and 3 were combined and redistilled through a micro Vigreaux column to give 10.5 g of ketone product, b.p. 87°-88° C. (2 mm).

EMBODIMENTS 9–11

Following procedures similar to those described in Embodiments 1–8 above, the following ketones of formula II in which X is =O, are prepared.
5,7,7-triethyl-6-oxabicyclo[3.2.2]nonan-4-one,
5-ethyl-7,7-dimethyl-6-oxabicyclo[3.2.2]nonan-4-one,
5-methyl-7,7-diethyl-6-oxabicyclo[3.2.2]nonan-4-one.

EMBODIMENT 12

5,7,7-Trimethyl-6-oxabicyclo[3.2.2]nonan-4-exo-ol

To a stirred mixture of 75 ml of 1M L-Selectride (lithium tri-sec-butylborohydride, 1M solution in tetrahydrofuran) and 100 ml of tetrahydrofuran held at −45° C. was added dropwise over one hour a solution of 10.5 g of the ketone of Embodiment 8 above in 50 ml of tetrahydrofuran. The cooling bath was removed and the mixture was allowed to warm slowly to 25° C. and remain there for one hour. After cooling to 5° C., there was added successively 10 ml of water, 28 ml of 6N sodium hydroxide and 42 ml of 30% hydrogen peroxide. Cooling was used to maintain the exothermic reaction below 30° C. After an additional 30 minutes at 25° C., the mixture was saturated with 80 g of anhydrous potassium carbonate and extracted three times with diethyl ether. The combined ether extracts was dried, filtered, vacuum-concentrated and distilled through a micro Vigreaux column to give 4.8 g of product, b.p. 67°-70° C. (0.4 mm).

EMBODIMENTS 13–16

Following procedures similar to those described in Embodiment 12 above, the following alcohols of formula II in which X is —OH, are prepared.
7,7-dimethyl-6-oxabicyclo[3.2.2]nonan-4-ol,
5,7,7-triethyl-6-oxabicyclo[3.2.2]nonan-4-ol,
5-methyl-7,7-diethyl-6-oxabicyclo[3.2.2]nonan-4-ol, and 5-ethyl-7,7-dimethyl-6-oxabicyclo[3.2.2]nonan-4-ol.

EMBODIMENT 17

4-exo-(Benzyloxy)-5,7,7-trimethyl-6-oxabicyclo[3.2.2-]nonane

A mixture of 5.7 g of the alcohol of Embodiment 12 above, 30 ml of N,N-dimethylacetamide and 1.6 g of 50% sodium hydride (washed with hexane) was warmed to 60°-70° C. for three hours. The cooled mixture was treated with 4.3 g of benzyl chloride and held at 65° C. for four hours. The cooled solution was poured into water and extracted three times with methylene chloride, and the combined methylene chloride extracts was washed, dried, concentrated and distilled through a micro Vigreaux column to give 3.3 g of product, b.p. 109°-112° C. (0.15 mm).

EMBODIMENTS 18-22

Following procedures similar to those described in Embodiment 17 above, the following compounds of formula I are prepared.
4-(2,6-dichlorobenzyloxy)-5,7,7-triethyl-6-oxabicyclo[3.2.2]nonane,
4-(2-fluorobenzyloxy)-5-methyl-7,7-diethyl-6-oxabicyclo[3.2.2]nonane,
4-(2-methylbenzyloxy)-5,7,7-trimethyl-6-oxabicyclo[3.2.2]nonane,
4-(tetrahydro-2-pyranylmethoxy)-6-oxabicyclo[3.2.2-]nonane, and
4-(2-chlorobenzyloxy)-5-ethyl-7,7-dimethyl-6-oxabicyclo[3.2.2]nonane.

EMBODIMENT 23

4-Hydroxy-4-methylcycloheptanecarboxylic Acid Lactone

To 200 ml of concentrated sulfuric acid stirred magnetically at 10°-15° C. was added dropwise 39.8 g of the Michael addition product from cyclopentanone and methyl vinyl ketone. After three days standing at 25° C., the mixture was poured onto 800 g of ice and extracted twice with methylene chloride, and the combined methylene chloride extracts was washed with saturated sodium bicarbonate, dried, concentrated at 70° C. and Claisen-distilled to give 23.0 g of product, b.p. 70°-80° C. (0.2 mm).

EMBODIMENT 24

Ethyl 4-Methyl-3-cycloheptenecarboxylate and Ethyl 4-Methyl-4-cycloheptenecarboxylate (Alternative Preparation)

A mixture of 18.6 g of the lactone from Embodiment 23 above, 200 ml of ethanol and 8 g of p-toluenesulfonic acid monohydrate was allowed to stir magnetically at reflux for seven hours and then stand overnight. To this mixture was added 4.2 g of anhydrous sodium acetate, and stirring was continued for 15 minutes. Concentration was carried out at 60° C. and the residue was dissolved in methylene chloride, washed with bicarbonate, dried, concentrated and distilled at 6 mm through a micro Vigreaux column to give two samples as follows: 6.5 g, of b.p. 94°-96° C. having a 46:41 isomer ratio and 5.2 g of b.p. 96°-101° C. having a 36:44 ratio of isomers. The two samples were combined to give 11.7 g of product.

EXAMPLES OF ACTIVITY WITH RESPECT TO PLANTS

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*
Mustard—*Brassica kaber*
Grain sorghum—*Sorghum vulgare* (Pioneer 265)
Corn—*Zea maize* (deKalb X363)
Cotton—*Gossypium hirsutum* (Acala SJ-2)
Soybean—*Glycine max* (Amsoy 71)
Wheat—*Triticum aestivum* (Cajeme 71)
Sugar beet—*Beta vulgaris*
Cocklebur—*Xanthum pennsylvanicum*

PRIMARY TESTS—PREEMERGENCE ACTIVITY

The preemergence (soil) activity of compounds of the invention was evaluated by planting seeds of barnyardgrass, garden cress, downy brome, velvetleaf, yellow foxtail, and sicklepod in test tubes, nominally measuring 25×200 mm, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 mg of the test compound per each tube containing the seeds of the other plants. The dosages were approximately 22 and 2.2 lb of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

PRIMARY TESTS—POSTEMERGENCE ACTIVITY

The postemergence (foliar) activity of compounds of the invention was evaluated by spraying 10-day-old large crabgrass plants, 13-day-old redroot pigweed plants, 6-day-old Johnsongrass plants, 9-day-old velvetleaf plants, 9-day-old yellow foxtail plants and 9-day-old sickle-pod plants to runoff with a liquid formulation of the test compound. The crabgrass and pigweed plants were sprayed with 2.4 ml of a 0.25% solution (about 10 lb of the test compound per acre), and other plants were sprayed with 2.4 ml of a 0.025% solution (about 1 lb of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence activity tests conducted on the compounds of the invention are set forth in Table 1.

optionally substituted by 1 or 2 chlorine or fluorine atoms or methyl groups.

3. A compound according to claim 2 wherein $R^1$, $R^2$ and $R^3$ each independently is a hydrogen atom, a methyl group or an ethyl group.

4. A compound according to claim 3 wherein $R^1$, $R^2$ and $R^3$ are the same.

5. A compound according to claim 4 wherein $R^1$, $R^2$ and $R^3$ are methyl groups.

6. A compound according to claim 5 wherein R is a 2-chlorophenyl group.

TABLE 1

| | HERBICIDAL ACTIVITY | | | | | | | | | | | |
|---|---|---|---|---|---|---|---|---|---|---|---|---|
| | Preemergence (Soil) | | | | | | Postemergence (Foliar) | | | | | |
| Embodiment | Barnyard Grass | Garden Cress | Downy Brome | Velvet Leaf | Yellow Foxtail | Sicklepod | Crab Grass | Pig Weed | Johnson Grass | Velvet Leaf | Yellow Foxtail | Sicklepod |
| 17 | 9 | 7 | 7 | 3 | 7 | 2 | 3 | 2 | 0 | 2 | 2 | 2 |

What is claimed is:

1. A compound of the formula I

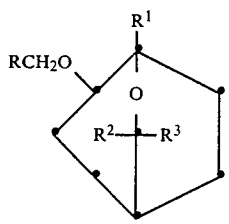

wherein $R^1$, $R^2$ and $R^3$ each independently is a hydrogen atom or an alkyl group containing from 1 to 10 carbon atoms and R is an ethynyl group, a cycloalkyl group containing from 3 to 10 carbon atoms, a cyclohexenyl group, a cyano group, a secondary alkyl group containing from 3 to 10 carbon atoms, a phenyl group optionally substituted by 1 or 2 chlorine or fluorine atoms or methyl groups, a naphthyl group, or heterocyclic group selected from a 2-pyridinyl, 2-pyrimidinyl, tetrahydro-2-pyranyl, imidazolyl, triazolyl, thiadiazolyl, 2-quinolinyl, 1-isoquinolinyl, pyrrolyl, N-methylimidazol-2-yl, N-methylpyrazol-2-yl, isoxazolyl, isoxazolyl, isothiazolyl, thiazolyl, thienyl, 5-methyl-2-furanyl or triazinyl group.

2. A compound according to claim 1 wherein R is an ethynyl group, a 2-pyridinyl group, or a phenyl group 7. A compound according to claim 5 wherein R is a 2-fluorophenyl group.

8. A compound according to claim 5 wherein R is a 2-methylphenyl group.

9. A compound according to claim 5 wherein R is a phenyl group.

10. A plant growth regulating composition comprising an effective amount of a compound according to claim 1 and at least one inert carrier or surface-active agent.

11. A method of regulating plant growth at a locus comprises applying to the locus or the plant an effective amount of a compound according to claim 1.

12. A method according to claim 11 wherein the plant growth is regulated by depressing growth of the plant or by killing the plant.

13. A compound according to claim 1 wherein R is ethynyl, phenyl, 2-chlorophenyl, 2-methylphenyl, naphthyl, 2-pyridinyl, 2-pyrimidinyl, tetrahydro-2-pyranyl, imidazolyl, triazolyl, thiadiazolyl, 2-quinolinyl, 1-isoquinolinyl, pyrrolyl, N-methylimidazol-2-yl, N-methylpyrazol-2-yl, isoxazolyl, oxazolyl, isothiazolyl, thiazolyl, thienyl, 5-methyl-2-furanyl, triazinyl, cyclopropyl, 1-methylcyclopropyl, cyano or cyclohexenyl.

14. A compound according to claim 13 wherein R is tetrahydro-2-pyranyl.

* * * * *